US011034640B1

(12) United States Patent
Micoine et al.

(10) Patent No.: US 11,034,640 B1
(45) Date of Patent: Jun. 15, 2021

(54) METHOD FOR THE CONTINUOUS PRODUCTION OF KETONES FROM EPOXIDES IN A FIXED BED

(71) Applicant: Evonik Operations GmbH, Essen (DE)

(72) Inventors: Kévin Micoine, Herten (DE); Luca Cameretti, Dortmund (DE); Ralf Meier, Dortmund (DE); Marcus Matthias Stergar, Herten (DE); Dominik Schulte-Althoff, Haltern am See (DE); Axel Prinz, Hanau (DE)

(73) Assignee: Evonik Operations GmbH, Essen (DE)

( * ) Notice: Subject to any disclaimer, the term of this patent is extended or adjusted under 35 U.S.C. 154(b) by 0 days.

(21) Appl. No.: 17/250,133

(22) PCT Filed: Jun. 3, 2019

(86) PCT No.: PCT/EP2019/064319
§ 371 (c)(1),
(2) Date: Dec. 4, 2020

(87) PCT Pub. No.: WO2019/233938
PCT Pub. Date: Dec. 12, 2019

(30) Foreign Application Priority Data

Jun. 7, 2018 (EP) ..................................... 18176493

(51) Int. Cl.
| | | |
|---|---|---|
| C07C 45/58 | (2006.01) | |
| C07D 225/02 | (2006.01) | |
| B01J 21/06 | (2006.01) | |
| B01J 21/08 | (2006.01) | |
| B01J 8/04 | (2006.01) | |
| B01J 23/44 | (2006.01) | |

(52) U.S. Cl.
CPC ............. *C07C 45/58* (2013.01); *B01J 8/0492* (2013.01); *B01J 21/066* (2013.01); *B01J 21/08* (2013.01); *B01J 23/44* (2013.01); *B01J 2208/025* (2013.01); *C07C 2521/06* (2013.01)

(58) Field of Classification Search
CPC ........ C07C 45/58; C07C 47/33; C07D 225/02
See application file for complete search history.

(56) References Cited

U.S. PATENT DOCUMENTS

| | | | |
|---|---|---|---|
| 9,000,223 | B2 | 4/2015 | Micoine et al. |
| 9,278,898 | B2 | 3/2016 | Cameretti et al. |
| 9,382,181 | B2 | 7/2016 | Cameretti et al. |
| 9,533,932 | B2 | 1/2017 | Micoine et al. |
| 9,533,933 | B2 | 1/2017 | Micoine et al. |
| 9,637,436 | B2 | 5/2017 | Micoine et al. |
| 9,643,153 | B2 | 5/2017 | Meier et al. |
| 2014/0166470 | A1 | 6/2014 | Cameretti et al. |
| 2014/0171636 | A1 | 6/2014 | Cameretti et al. |
| 2014/0249331 | A1 | 9/2014 | Micoine et al. |
| 2015/0328619 | A1 | 11/2015 | Meier et al. |
| 2016/0031783 | A1 | 2/2016 | Micoine et al. |
| 2016/0031784 | A1 | 2/2016 | Micoine et al. |
| 2016/0096794 | A1 | 4/2016 | Micoine et al. |
| 2017/0095789 | A1 | 4/2017 | Meier et al. |
| 2019/0177478 | A1 | 6/2019 | Micoine et al. |
| 2019/0232271 | A1 | 8/2019 | Meier et al. |
| 2019/0345101 | A1 | 11/2019 | Cameretti et al. |

FOREIGN PATENT DOCUMENTS

| | | |
|---|---|---|
| EP | 2772478 | 9/2014 |
| EP | 3002058 | 4/2016 |
| EP | 3 498 758 | 6/2019 |

OTHER PUBLICATIONS

U.S. Appl. No. 15/382,991, filed Dec. 19, 2016, 2017/0095789, Meier et al.
U.S. Appl. No. 16/312,173, filed Dec. 20, 2018, 2019/0232271, Meier et al.
U.S. Appl. No. 16/216,143, filed Dec. 11, 2018, 2019/0177478, Micoine et al.
U.S. Appl. No. 16/482,981, filed Aug. 1, 2019, 2019/0345101, Cameretti et al.
European Search Report dated Nov. 16, 2018 in European Application No. 18176493.7.
International Search Report dated Jul. 29, 2019 in PCT/EP2019/064319 with English translation, 5 pages.
Written Opinion dated Jul. 29, 2019 in PCT/EP2019/064319 with English Translation, 9 pages.

*Primary Examiner* — Sikarl A Witherspoon
(74) *Attorney, Agent, or Firm* — Grüneberg and Myers PLLC

(57) ABSTRACT

A method is useful for the continuous production of ketones from a compound with at least one epoxide group in at least one fixed bed reactor. A catalyst composition is used with at least one noble metal and at least one metal oxide. To reduce the proportions of high-boilers which form in the reaction, an inert gas is introduced so that a carbon monoxide partial pressure of 50 mbar or less is set in the reactor.

13 Claims, 2 Drawing Sheets

METHOD FOR THE CONTINUOUS PRODUCTION OF KETONES FROM EPOXIDES IN A FIXED BED

CROSS-REFERENCE TO RELATED APPLICATIONS

This application is the National Stage entry under § 371 of International Application No. PCT/EP2019/064319, filed on Jun. 3, 2019, and which claims the benefit of European Application No. 18176493.7, filed on Jun. 7, 2018. The content of each of these applications is hereby incorporated by reference in its entirety.

The present invention relates to a continuous method for producing ketones from epoxides in a device having at least one fixed bed reactor.

Methods for ketone production from epoxides are already known in the prior art. Continuous processes are frequently used for obtaining ketones in this context. The ketones obtained are often used as starting products for further reactions.

In the continuous production of ketones from epoxides, by-products often form having a higher boiling point than the desired ketones. They reduce the yield of ketone and have to be laboriously removed.

EP 2743247 A1 (US 2014/0171636 A1) describes a method for removing high boilers. which can be effected by means of a sequence of two or more side offtake columns.

EP 2742981 A2 (US 2014/0166470 A1) describes a separation process for high boilers in which a column with a perforated side wall is used.

The prior art thus discloses solutions for removing the high boiler by-products formed. Not mentioned, however, are methods which significantly reduce the proportions of high boilers during the reaction to the ketone.

The object therefore consisted of providing a method of the type mentioned at the outset. which allows the proportion of high boilers to be kept low during the reaction of epoxides to ketones. As a result, the yield of ketones should increase and the apparatus complexity for removing high boilers should be reduced.

Surprisingly, it has been found that the proportion of high boilers can be kept low when the partial pressure of carbon monoxide remains low. In this case hydrogen is not present or is present in small amounts, i.e. at a hydrogen partial pressure of at most 0.2 bar. Accordingly, a method is provided for the continuous production of ketones from a compound comprising at least one epoxide group. The method is carried out in a device comprising at least one fixed bed reactor, also referred to below as reactor, for short, wherein the at least one fixed bed reactor contains a catalyst composition comprising at least one noble metal and at least one metal oxide. In this case, the pressure in the reactor upstream of the catalyst is at least 1.2 bar. The gas phase of the reactor has a maximum 0.2 bar hydrogen partial pressure; the pressure is preferably 0 bar, i.e. there is no hydrogen present. A carbon monoxide partial pressure of 50 mbar or less, preferably 30 mbar or less, in the gas phase downstream of the catalyst, is set in the fixed bed reactor by introducing at least one inert gas.

DETAILED DESCRIPTION OF THE INVENTION

Figure 1:
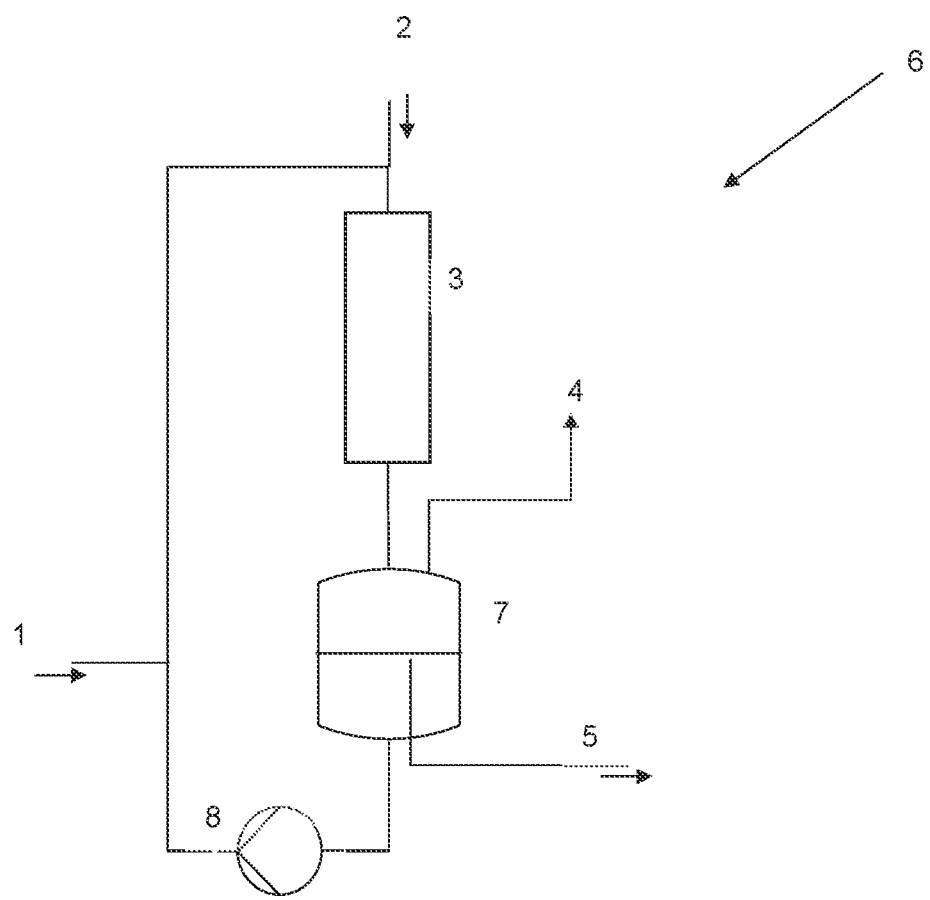
FIG. 1 shows a device having a circulation reactor.

The inert gas is typically introduced upstream of the fixed bed reactor.

In a continuous process, carbon monoxide is continuously produced and a certain partial pressure of carbon monoxide is set depending on the pressure of the system and on the dilution by inert gases. The partial pressure of carbon monoxide can stabilize at a comparatively high level, particularly in an industrial production plant since, owing to industrial constraints (for example pressure loss over the catalyst, pressure level in the offgas line), the total pressure in the reactor above the catalyst is a minimum of 1.2 bar and the introduction of inert gases (e.g. nitrogen) is restricted for economic reasons. Although an increase in the total pressure in the reactor and a reduction of the introduction of inert gases into a production plant would at first sight be advantageous economically and technically, it has been found here that control of these parameters is necessary in order to keep the partial pressure of carbon monoxide low.

The partial pressure of carbon monoxide can be lowered by diluting the gas phase of the fixed bed reactor with an inert gas, optionally in combination with lowering the total pressure in the reactor. In particular, control of the partial pressure of carbon monoxide can considerably reduce the formation of high-boiling by-products and can therefore significantly increase the yield of utilizable products.

The compound comprising at least one epoxide group is referred to below as compound E.

The inert gases include, for example, nitrogen, carbon dioxide, sulfur hexafluoride and noble gases such as helium and argon. Preferred inert gases are nitrogen, carbon dioxide, argon or mixtures thereof. Preferred inert gases are nitrogen, carbon dioxide, argon or mixtures thereof, particularly preferably nitrogen. The ratio of the amount of inert gas or gas mixture to the amount of compound E is preferably at least 0.5, preferably 1 and particularly preferably 2.

The partial pressure of carbon monoxide can additionally be reduced by reducing the total pressure in the reactor. The total pressure in the reactor above the catalyst is preferably less than 4 bar, particularly preferably less than 2 bar, especially preferably less than 1.5 bar.

The compound E can be aliphatic or cycloaliphatic, with cycloaliphatic compounds being preferred. Preferably, 4 to 20 carbon atoms, preferably 6 to 16 carbon atoms, particularly preferably 8 to 14 carbon atoms, especially preferably 10 to 12 carbon atoms and in particular 12 carbon atoms are comprised.

The compound E can contain one or more epoxide groups, with monoepoxide compounds being preferred.

Furthermore, the compound can be saturated or unsaturated. For example, one or two double bonds can be present.

Preferred compounds E are monoepoxycycloalkanes, monoepoxycycloalkanedienes and monoepoxycycloalkenes, with monoepoxycycloalkanes being particularly preferred. A very particularly preferred compound E is monoepoxycyclododecane.

During the continuous conversion of epoxides to ketones, by-products can form. Some of these by-products have a boiling point so high that they cannot be detected by gas chromatography. The formation of such by-products represents a loss of selectivity. In order to take into account all possible impurities in the calculation of the selectivity, the reaction mixtures were analysed by gas chromatography (GC) with addition of a known amount of tetradecane as external standard. For all known substances present in the reaction of, for example, epoxycyclododecane (tetradecane, cycloundecane, cycloundecene, cyclododecane, cyclododecene, cyclododecanone, cyclododecanol, epoxycyclododecane), GC factors can be determined using recognized reference solutions. Consequently, a mass-based proportion for each substance in each reaction mixture can be calculated by adding a known amount of tetradecane to each reaction sample. The proportions of all substances which are visible in the chromatogram can be calculated from the GC chromatogram. The proportion of high-boiling by-products (high boilers) which are not detected in the GC can be calculated by the difference between 100% and the sum total of all substances in the GC chromatogram.

High boilers include those reaction products of the compound comprising at least one epoxide group which have a higher boiling point of at least 10K at 1013 hPa compared to the ketone formed. They cannot be converted by further processes to the desired ketone (non-utilizable products). In the case of epoxycyclododecane, the high boilers include, for example, cyclododecan-1-on-2-ol, cyclododecan-1,2-diol, C12-dimers (i.e. compounds having 24 carbon atoms), C12-trimers (i.e. compounds having 36 carbon atoms) and further oligomers. By contrast, by-products are obtained that are utilizable products such as the alkane, the alkene, the alkenone, the alcohol and the alkenol, which can be converted to the desired ketone (utilizable products) by known methods of the prior art, and therefore do not represent any loss of selectivity. In the case of epoxycyclododecane, these include cyclododecane (CDAN), cyclododecene (CDEN), cyclododecanone (CDON), cyclododecenone (CDENON), cyclododecanol (CDOL) and cyclododecenol (CDENOL).

Since the high-boiling by-products represent unusable waste, the proportion thereof should be as low as possible. This proportion is preferably less than 5% by weight, particularly preferably less than 2% by weight, based on the epoxide converted.

Surprisingly, it has been found that carbon monoxide is formed as by-product during the conversion of epoxides to ketones and, in the continuous process, represents a significant proportion of the gas phase of the reactor. The formation of carbon monoxide can be explained, for example in the case of epoxycyclododecane, by the secondary reaction to cycloundecane and cycloundecene. Based on epoxycyclododecane, 1 to 2 mol % cycloundecane and cycloundecene can form during the reaction, which corresponds to formation of 1 to 2 mol % CO. Depending on the amount of gas metered into the plant, the carbon monoxide proportion can consequently correspond to quite a few percent of the gas phase.

The partial pressure of carbon monoxide is calculated from the proportion of carbon monoxide in the gas phase and the total pressure. The proportion of carbon monoxide may be determined, for example, by FT-IR spectrometry online using a probe. It has been found in this case that this partial pressure, in the absence of hydrogen or under low hydrogen partial pressures of up to 0.2 bar, has a considerable influence on the selectivity of the chemical reaction. A relatively high partial pressure of carbon monoxide results in a reduction of the ketone selectivity and an increase in the proportion of high boilers. This effect is reversible and the ketone selectivity improves as the CO partial pressure is further reduced. A possible explanation is poisoning of the noble metal-containing catalyst by carbon monoxide, which inhibits the desired reaction path to the ketone.

If enough hydrogen is introduced into the reactor, this poisoning of the noble metal-containing catalyst is not observed: the proportion of high boilers is not elevated, even at higher concentrations of carbon monoxide. However, it is preferable to omit the introduction of hydrogen in industrial processes because it results in a lower selectivity for the ketone and an increased selectivity for the alcohol and alkane by-products. For these reasons, the method according to the invention is limited to a hydrogen partial pressure of at maximum 0.2 bar.

The temperature during the reaction is preferably adjusted to a range from 100 to 350° C., preferably 150 to 250° C. and particularly preferably between 180 and 230° C. The reaction can be carried out with a compound E, which is in the liquid or gaseous state.

The continuous rearrangement of epoxides to ketones in a fixed bed reactor is preferably effected in the presence of a noble metal-containing catalyst (catalyst system), wherein the catalyst preferably comprises titanium dioxide, zirconium dioxide or both.

The noble metal of the catalyst system is preferably selected from ruthenium, rhodium, palladium, osmium, iridium and platinum, with ruthenium, palladium and platinum being preferred and palladium being particularly preferred. The noble metal can be present as powder (unsupported) or in supported form. Suitable in powder form are, for example, elemental noble metals or oxides thereof.

Furthermore, at least one metal oxide can be present as further constituent of the catalyst system. The metal oxide of the catalyst system comprises titanium dioxide, zirconium dioxide or mixtures thereof or consists of at least one of the oxides specified above. For example the metal oxide of the catalyst system may comprise a mixed oxide, wherein the mixed oxide comprises zirconium dioxide and silicon dioxide.

The metal oxide of the catalyst system can function as support for the noble metal of the catalyst system. The noble metal can optionally be applied to an alternative support selected, for example, from aluminium oxide, silicon dioxide or activated carbon. Preferred supports are titanium dioxide, zirconium dioxide or mixed oxides comprising zirconium dioxide.

The metal oxides of the catalyst system and the alternative supports can be present as powder or as mouldings. Suitable mouldings are beads, extrudates, tablets, granules and pellets. It is preferable that the support of the noble metal is present as a moulding. It is likewise preferable that the metal oxide of the catalyst system, if it does not function as a support, is present as a moulding.

The catalyst system can be present mutually independently as one of the following system forms:
  I) The noble metal is supported on a metal oxide selected from titanium dioxide and zirconium dioxide, wherein preferably no titanium dioxide is present.
  II) The noble metal is supported, wherein the support does not comprise or consist of titanium dioxide and/or zirconium dioxide. The system additionally comprises at least one metal oxide selected from titanium dioxide or zirconium dioxide.

Suitable titanium dioxide as metal oxide of the catalyst system can be obtained by the sulfate process, the chloride process or by flame hydrolysis (pyrogenic process) of titanium tetrachloride. All methods are known to a person skilled in the art. Suitable modifications are rutile and anatase, wherein the titanium dioxide used may comprise mixtures of the modifications specified.

Particularly preferred titanium dioxide is obtained by flame pyrolysis, as described, for example, in DE-C-830786.

Suitable titanium dioxide is obtainable under the name Aeroxide P25 titanium dioxide (powder) or Aerolyst 7711 (moulding) from Evonik, Germany, and Hombikat M234 (moulding) from Sachtleben, Germany.

Zirconium dioxide (zirconium(IV) oxide) is obtainable for example from zirconium hydroxide, which has been calcined at over 200° C., for example at 350° C.

Mixed oxides particularly suitable as metal oxide include zirconium dioxide and silicon dioxide or consist of these two oxides. The proportion of the sum of zirconium dioxide and silicon dioxide in the mixed oxide is preferably at least 20% by weight and preferably at least 30% by weight, particularly preferably 50% by weight and especially preferably 95% by weight, based in each case on the total weight of the mixed oxide. The mixed oxide particularly preferably consists of zirconium dioxide and silicon dioxide. The mass ratio of zirconium dioxide to silicon dioxide in the mixed oxide is preferably from 86:14 to 99.9:0.1.

Mixed oxides can be formed from calcination of a zirconium compound with a silicon dioxide. Preferably, the silicon dioxide is produced by means of pyrogenic methods. The process is known to the person skilled in the art, e.g. from the series of papers "Fine Particles" No. 11 (7th edition, 2003), company journal of Degussa AG. The zirconium compound is preferably selected from zirconium dioxide, zirconium hydroxide, zirconium acetate, zirconium nitrate, zirconium oxychloride, ammonium zirconium carbonate or mixtures thereof. Preference is given to using zirconium dioxide, zirconium hydroxide or mixtures thereof. Zirconium hydroxide is understood as meaning zirconium(IV) hydroxide.

The metal oxide of the catalyst system can have an average bulk density of 0.5 to 2 $g/cm^3$. The bulk density is measured by firstly weighing an empty 1000 ml measuring cylinder. The metal oxide is then poured in up to the 500 ml mark. The filled cylinder is weighed again, the weight difference between the filled and empty measuring cylinder giving the bulk density of the material in $g/cm^3$.

The metal oxide of the catalyst system preferably has a BET surface area which is in the range of 5-155 $m^2/g$.

It is preferred that the BET surface area of the metal oxide of the catalyst systems according to the invention is in a range from 80 to 150 $m^2/g$. The BET surface area is measured in accordance with DIN 66131 and DIN ISO 9277. A BET surface area above 155 $m^2/g$ leads to a lower selectivity.

The fraction of noble metal, based on the total weight of noble metal and support, can be 0.01 to 5% by weight, preferably 0.05 to 1.2% by weight and preferably 0.1 to 0.6% by weight.

The noble metal can be distributed on or within the support.

The quantitative fraction of noble metal, based on the quantitative amount of compound E can be 0.00001 to 0.1, preferably 0.0001 to 0.01.

The quantitative fraction of metal oxide in the catalyst system, based on the quantitative amount of compound E, can be 0.01 to 100, preferably 0.01 to 10.

To produce system II, the noble metal can be impregnated on an inert support, where the support does not consist of the metal oxide. The support preferably does not comprise or consist of the metal oxide. For this purpose, every impregnation method known to the person skilled in the art can be used, such as the application of a noble metal solution to the support.

To produce system I, the noble metal can be impregnated on the metal oxide as support. For this purpose, every impregnation method known to the person skilled in the art can be used, such as the application of a noble metal solution to the support.

The method according to the invention can be carried out at a partial hydrogen pressure of from 0 up to 0.2 bar and preferably from 0 up to 0.1 bar. The process according to the invention is preferably carried out without hydrogen.

The pressure data specified above refer to the partial pressure of hydrogen in the system. Usually, components of the reaction mixture, including of the solvent, air or inert gases, are further gaseous constituents of the system.

The method is conducted in at least one fixed bed reactor. Alternatively, at least one further fixed bed reactor is connected downstream to the fixed bed reactor. The offgas of the fixed bed reactors (including of the first fixed bed reactor) can either be fed to a further reactor or be removed from the system.

If the method comprises two or more reactors connected one after another in series, fresh gas can be introduced into each reactor (so-called cross current operation). Alternatively, fresh gas can be introduced into a reactor, the offgas of which is in turn introduced into the next reactor. As a result, the carbon monoxide is diluted in each reactor (so-called co-current operation). Preferably, gas is introduced in countercurrent: Fresh gas is introduced into the last reactor and the gas stream is subsequently fed to the preceding reactor, and so on up to the first reactor, the offgas of which is discharged from the process. As a result, the total amount of fresh gas required can be reduced. A combination of crosscurrent, co-current and countercurrent operation may also alternatively be selected.

The fixed bed reactor is at least partly filled with the noble metal-containing catalyst system. The catalyst located therein is also referred to as a catalyst bed. The reactor may be operated, for example, as a circulation reactor or as a tubular reactor ("plug flow"). The reaction mixture (liquid phase and gas phase) is passed through the reactor, for example using a pump, and is thus brought into contact with the catalyst. After the reactor, the liquid phase and the gas phase are separated and at least a portion of the gas phase is discharged from the system through an offgas conduit. A certain mass feed comprising the epoxide is metered continuously prior to the reactor or into the circuit and the same mass of reaction mixture after the reactor or from the circuit is discharged such that the mass of the reaction mixture in the system remains constant. In addition, one or more gases, such as nitrogen, argon and hydrogen for example, can be metered into the system. Preferably, this metered addition takes place prior to the fixed bed reactor. The pressure in the reactor can be adjusted, for example, by a supply pressure regulator in the offgas line.

FIG. 1 shows a device (6) having a circulation reactor, i.e. a fixed bed reactor (3) which is operated in a closed loop. The feed (1) is introduced into the system at this point. Inert gas (2) is metered in prior to the fixed bed reactor(s) (3) comprising the catalyst system. Offgas (4) and the liquid product mixture (5) are separated in a separator (7). The offgas is removed from the system. The product mixture is in part fed back to the fixed bed reactor(s) and in part to the next method step. The pressure in the device (6) is increased by a pump (8). The pressure between the pump and catalyst, which is located in the fixed bed reactor (3), is generally elevated compared to other regions of the device. This corresponds to the aforementioned pressure in the reactor upstream of the catalyst which is at least 1.2 bar.

Figure 2:
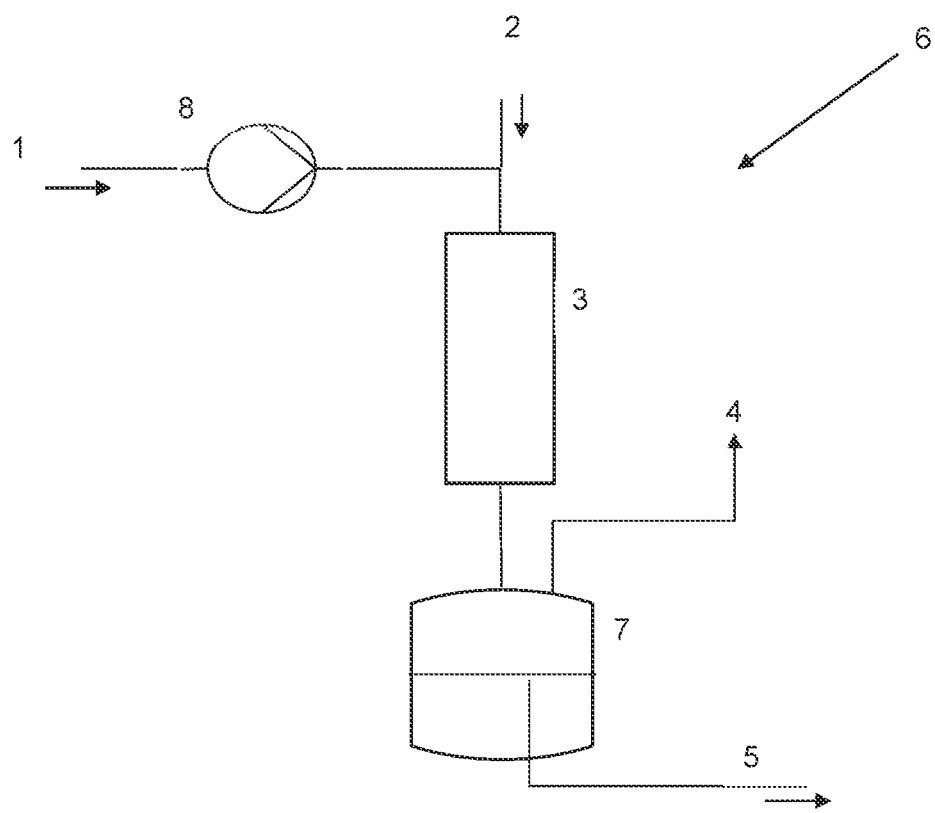
FIG. 2 shows a device having a pump and tubular reactor as the fixed bed reactor.

A device (6) having a pump (8) and a tubular reactor as the fixed bed reactor (3) is depicted in FIG. 2 in which the feed (1) is fed and inert gas (2) is added prior to the fixed bed reactor (3). Offgas (4) and product (5) are separated in the separator (7).

The process according to the invention can be carried out in organic solvents, it being preferred to work without solvents and thus to use no organic solvents. Suitable solvents are, for example, alkanes such as n-hexane, n-heptane, n-tetradecane and cyclohexane; ethers such as tetrahydrofuran and dioxane; alkanols such as methanol, ethanol and t-butanol; esters such as ethyl acetate and butyl acetate. The solvents can be used on their own or in mixtures. The solvent is preferably used in an amount which is 20 times or less than, preferably 10 times or less than, the weight of compound E.

In a preferred embodiment of the invention, monoepoxycyclododecane is converted continuously to cyclododecanone with a fixed bed catalyst without solvent at temperatures of 170 to 250° C., wherein the partial pressure of carbon monoxide in the gas phase of the reactor is controlled downstream of the catalyst below 50 mbar. The partial pressure of carbon monoxide is determined, for example, by measuring the total pressure using a manometer and by measuring the proportion of carbon monoxide by means of FT-IR spectrometry.

The invention further provides a process for the synthesis of lactams (lactam process according to the invention), in which the aforementioned process according to the invention for producing ketones is used: firstly, rearrangement of a compound (compound E) comprising at least one epoxide group to the ketone takes place. Then, oximation of the ketone to the oxime is carried out. Subsequently, Beckmann rearrangement of the oxime to the lactam takes place. The compound E is preferably selected from aliphatic monoepoxycycloalkanes, aliphatic monoepoxycycloalkanedienes and aliphatic monoepoxycycloalkenes, with monoepoxycycloalkanes being preferred.

If the ketone is present in a mixture with the corresponding alcohol derivative, a dehydrogenation of the alcohol to the ketone can take place. The Beckmann rearrangement may be carried out using sulphuric acid or cyanuric chloride. The lactams may be subjected to further processing by polycondensation to give polyamides.

The dehydrogenation, the oximation, the Beckmann rearrangement and the condensation reaction are known to the person skilled in the art.

In a preferred embodiment of the lactam process according to the invention, laurolactam is prepared from monoepoxycyclododecane (or cyclododecane epoxide or 1,2-cyclododecane epoxide).

In the context of the preferred lactam method, monoepoxycyclododecane is obtainable by the following reaction steps: 1,3-butadiene is reacted to give cyclododecatriene by cyclotrimerization. This is followed by a hydrogenation to give the cyclododecene. The cyclododecane epoxide is obtained by subsequent epoxidation. The person skilled in the art in the field of the synthesis of organic compounds can prepare other aliphatic and cycloaliphatic compounds E analogously to the synthesis of monoepoxycyclododecane.

The present invention is more particularly elucidated hereinbelow with reference to examples. Alternative embodiments of the present invention are obtainable analogously.

LIST OF REFERENCE NUMERALS

1 Feed
2 Inert gas
3 Fixed bed reactor
4 Offgas
5 Product
6 Device
7 Separator
8 Pump

EXAMPLES

The percentages in the case of catalysts give the weight fraction of the noble metal, based on the total weight of the catalyst comprising noble metal and support. The abbreviation "calc." stands for "calcined". The abbreviations for the substances are: CDAN: Cyclododecane; CDEN: Cyclododecene; ECD: Epoxycyclododecane; CDON: Cyclododecanone; CDENON: Cyclododecenone (isomer mixture); CDOL: Cyclododecanol; CDENOL: Cyclododecenol (isomer mixture).

The catalyst system used consisted of a $ZrO_2$—$SiO_2$ mixed oxide (95% $ZrO_2$, 5% $SiO_2$) and a 0.5% Pd/$SiO_2$ catalyst. Both catalysts were produced in accordance with EP3006107 (mixed oxide corresponding to Example B and Pd/$SiO_2$ corresponding to Example D).

Gas chromatography (GC): Gas chromatographic investigations were carried out using a GC-2010 (Shimadzu) chromatograph, fitted with autosampler, flame ionization detector (FID), and GC capillary column Supelcowax® (60 m×0.32 mm×0.25 μm, Supelco). Measurements were carried out in the split mode (Split rate 1:66) with helium as carrier gas (flow rate 0.89 ml/min, linear carrier gas rate 17.9 cm/s). Temperature programme for GC oven: Start temperature 150° C.; heat to 180° C. at 5° C./min, hold for 10 min; heat to 200° C. at 5° C./min, hold for 10 min. Detector and injector temperatures were 340° C. and 220° C.

By adding an external standard (tetradecane) to each sample and applying the factor method, the composition of the reaction mixture was calculated in % by weight. Using the molar mass of each substance, the composition of the mixture could then be calculated in mol %. The conversion of the epoxide could then be calculated. The selectivity of each product was calculated on the basis of the difference in concentration of this product in the reaction mixture and in the reactant, based on the reacted epoxide. For the high boilers, the selectivity was calculated on the basis of the molar mass of the epoxide, which provides a statement about the amount of epoxide which had been converted to high boilers (loss of selectivity during the reaction).

The proportion of carbon monoxide was determined by IR spectrometry by introducing the offgas from the reactor into an IR spectrometer. The spectroscopic measurements were carried out using a Gasmet DX4000 Fourier transform (FT) mid-IR spectrometer from Ansyco, which records the absorption in the spectral range of 600-4200 $cm^{-1}$. The gaseous material stream from the reactor was fed via appropriate lines to the measurement cell of the spectrometer and secured by means of a Swagelok fitting. To avoid condensation in the material stream, the lines were heated to 110° C. by means of electrical trace heating. In the mid-IR spectrometer used, a ceramic Si—C material (Globar) served as mid-IR source. The measurement cell had a volume of 0.45 L and an optical path length of 500 cm, which was accomplished via multiple reflections. The measurement cell was also heated to a temperature of 110° C. A thermoelectrically cooled MCT detector served as detector. The CO determination was calibrated by reference spectra starting from test gases (range: 0.9 to 7 vol % carbon monoxide in nitrogen). For this purpose, the spectral range of the CO signal from 1850-2060 cm$^{-1}$ was evaluated, since no interferences with other components were observed here. The calibration and the measurements were carried out using the Calcmet software from Ansyco. The measurements of the gas phase of the reactor were carried out against pure nitrogen as background spectrum. The measurement durations used were 60 s with a measurement interval of 1800 s.

The figures for the mass flow of the nitrogen are specified for differentiation to the volume flow rate in NL/h. DIN 1343 is used as standard (back pressure 1013.25 mbar, gas temperature 0° C.).

Example 1: Non-Inventive

The reaction was carried out in a laboratory scale plant. The system consisted of two fixed-bed reactors in series (ca. 200 ml per reactor) and a storage container (1 L). The lower fixed bed reactor was filled with 45 g of $ZrO_2$—$SiO_2$ mixed oxide (95% $ZrO_2$, 5% $SiO_2$) and the upper fixed bed reactor with 90 g of 0.5% $Pd/SjO_2$. The container was filled with 1000 g of cyclododecanone. The liquid was pumped in a cycle from the storage container through the catalyst bed back to the storage container using a circulating pump (10 l/h). The reactors were heated to an interal temperature of 185° C. in the reaction mixture using a thermostat.

Then, 65 g/h of feed comprising 85.4% by weight epoxycyclododecane, 9.3% by weight CDAN and 5.3% CDEN were metered continuously into the circuit. This corresponds to a metered addition of 0.31 mol/h of epoxycyclododecane. Product was discharged continuously from the system via an overflow tube such that the fill level in the storage container remained constant. In addition, 2 NL/h of nitrogen were metered continuously into the system, which corresponds to an amount of 0.08 mol/h of $N_2$. Thus, the ratio of the amount of nitrogen to the amount of epoxycyclododecane was 0.26. Using a supply pressure regulator, a total pressure in the system of 3.2 bar was set and the offgas was discharged continuously from the system.

After a run time of 48 h, the reaction mixture was in steady state. A conversion of the epoxide of 77% was achieved. The selectivity for CDON was only 6.8 mol % and 17 mol % of high boilers were formed.

The proportion of carbon monoxide in the offgas was determined by IR spectrometry and was 2.6 mol %. At a total pressure of 3.2 bar, a partial pressure of carbon monoxide of 83 mbar was attained.

TABLE 1

Conversion of epoxide (mol %, GC with external standard) and selectivity for various products (mol %, GC with external standard)

| Conversion of epoxide (mol %) | Selectivity (mol %) | | | | | | |
|---|---|---|---|---|---|---|---|
| | Cyclo-undecane + cyclo-undecene | CDAN | CDEN | CDON | CDENON | CDOL | CDENOL | High boilers |
| 77 | 0.2 | 0.1 | 6.5 | 6.8 | 8.3 | 1.0 | 60.1 | 17 |

CDAN, CDEN, CDON, CDENON, CDOL and CDENOL are substances which can all be converted to CDON by known methods. They are therefore all utilizable products. On this basis, the selectivity for utilizable products is 82.8 mol %.

Example 2: Non-Inventive

The reaction was carried out in a laboratory scale plant in accordance with Example 1. 65 g/h of feed comprising 85.4% by weight epoxycyclododecane, 9.3% by weight CDAN and 5.3% CDEN were metered continuously into the circuit. This corresponds to a metered addition of 0.31 mol/h of epoxycyclododecane. Product was discharged continuously from the system via an overflow tube such that the fill level in the storage container remained constant. In addition, 5 NL/h of nitrogen were metered continuously into the system, which corresponds to an amount of 0.20 mol/h of $N_2$. Thus, the ratio of the amount of nitrogen to the amount of epoxycyclododecane was 0.67. Using a supply pressure regulator, a total pressure in the system of 3.2 bar was set and the offgas was discharged continuously from the system.

After a run time of 48 h, the reaction mixture was in steady state. A conversion of the epoxide of 78% was achieved. The selectivity for CDON was 37 mol % and 16.5 mol % of high boilers were formed.

The proportion of carbon monoxide in the offgas was determined by IR spectrometry and was 1.83 mol %. At a total pressure of 3.2 bar, a partial pressure of carbon monoxide of 59 mbar was attained.

TABLE 2

Conversion of epoxide (mol %, GC with external standard) and selectivity for various products (mol %, GC with external standard)

| Conversion of epoxide (mol %) | Cyclo-undecane + cyclo-undecene | CDAN | CDEN | CDON | CDENON | CDOL | CDENOL | High boilers |
|---|---|---|---|---|---|---|---|---|
| | | | | Selectivity (mol %) | | | | |
| 78 | 1.0 | 0,1 | 2.0 | 37.4 | 11.3 | 3.4 | 28.3 | 16.5 |

The selectivity for utilizable products was 82.5 mol %.

Example 3: Inventive

The reaction was carried out in a laboratory scale plant in accordance with Example 1. 65 g/h of feed comprising 85.4% by weight epoxycyclododecane, 9.3% by weight CDAN and 5.3% CDEN were metered continuously into the circuit. This corresponds to a metered addition of 0.31 mol/h of epoxycyclododecane. Product was discharged continuously from the system via an overflow tube such that the fill level in the storage container remained constant. In addition, 20 NL/h of nitrogen were metered continuously into the system, which corresponds to an amount of 0.81 mol/h of $N_2$. Thus, the ratio of the amount of nitrogen to the amount of epoxycyclododecane was 2.6. Using a supply pressure regulator, a total pressure in the system of 3.2 bar was set and the offgas was discharged continuously from the system.

After a run time of 48 h, the reaction mixture was in steady state. A conversion of the epoxide of 79% was achieved. The selectivity for CDON was 90 mol % and only 2 mol % of high boilers were formed.

The proportion of carbon monoxide in the offgas was determined by IR spectrometry and was 0.85 mol %. At a total pressure of 3.2 bar, a partial pressure of carbon monoxide of 27 mbar was attained.

TABLE 3

Conversion of epoxide (mol %, GC with external standard) and selectivity for various products (mol %, GC with external standard)

| Conversion of epoxide (mol %) | Cyclo-undecane + cyclo-undecene | CDAN | CDEN | CDON | CDENON | CDOL | CDENOL | High boilers |
|---|---|---|---|---|---|---|---|---|
| | | | | Selectivity (mol %) | | | | |
| 79 | 1.4 | 0.5 | 0.1 | 89.9 | 3.6 | 1.4 | 1.1 | 2.0 |

The selectivity for utilizable products was 97.6 mol %.

Example 4: Inventive

The reaction was carried out in a laboratory scale plant in accordance with Example 1. 65 g/h of feed comprising 85.4% by weight epoxycyclododecane, 9.3% by weight CDAN and 5.3% CDEN were metered continuously into the circuit. This corresponds to a metered addition of 0.31 mol/h of epoxycyclododecane. Product was discharged continuously from the system via an overflow tube such that the fill level in the storage container remained constant. In addition, 5 NL/h of nitrogen were metered continuously into the system, which corresponds to an amount of 0.20 mol/h of $N_2$. Thus, the ratio of the amount of nitrogen to the amount of epoxycyclododecane is 0.67. Using a supply pressure regulator, a total pressure in the system of 1.2 bar was set and the offgas was discharged continuously from the system.

After a run time of 48 h, the reaction mixture was in steady state. A conversion of the epoxide of 78% was achieved. The selectivity for CDON was 89 mol % and only 2.7 mol % of high boilers were formed.

The proportion of carbon monoxide in the offgas was determined by IR spectrometry and was 1.71 mol %. At a total pressure of 1.2 bar, a partial pressure of carbon monoxide of 21 mbar was attained.

TABLE 4

Conversion of epoxide (mol %, GC with external standard) and selectivity for various products (mol %, GC with external standard)

| Conversion of epoxide (mol %) | Cyclo-undecane + cyclo-undecene | CDAN | CDEN | CDON | CDENON | CDOL | CDENOL | High boilers |
|---|---|---|---|---|---|---|---|---|
| 77 | 1.5 | 0.8 | 0.1 | 88.5 | 5.2 | 0.1 | 1.0 | 2.9 |

The selectivity for utilizable products was 95.6 mol %.

Example 5: Inventive

The reaction was carried out in a laboratory scale plant in accordance with Example 1. 65 g/h of feed comprising 85.4% by weight epoxycyclododecane, 9.3% by weight CDAN and 5.3% CDEN were metered continuously into the circuit. This corresponds to a metered addition of 0.31 mol/h of epoxycyclododecane. Product was discharged continuously from the system via an overflow tube such that the fill level in the storage container remained constant. In addition, 20 NL/h of nitrogen were metered continuously into the system, which corresponds to an amount of 0.81 mol/h of $N_2$. Thus, the ratio of the amount of nitrogen to the amount of epoxycyclododecane is 2.6. Using a supply pressure regulator, a total pressure in the system of 1.2 bar was set and the offgas was discharged continuously from the system.

After a run time of 48 h, the reaction mixture was in steady state. A conversion of the epoxide of 76% was achieved. The selectivity for CDON was 90 mol % and only 2.3 mol % of high boilers were formed.

The proportion of carbon monoxide in the offgas was determined by IR spectrometry and was 0.70 mol %. At a total pressure of 1.2 bar, a partial pressure of carbon monoxide of 8 mbar was attained.

TABLE 5

Conversion of epoxide (mol %, GC with external standard) and selectivity for various products (mol %, GC with external standard)

| Conversion of epoxide (mol %) | Cyclo-undecane + cyclo-undecene | CDAN | CDEN | CDON | CDENON | CDOL | CDENOL | High boilers |
|---|---|---|---|---|---|---|---|---|
| 76 | 1.6 | 0.5 | 0.1 | 90,2 | 3.6 | 1.0 | 0.7 | 2.3 |

The selectivity for utilizable products was 96.1 mol %.

Result

It could be demonstrated by Examples 1 to 5 that reducing the CO partial pressure to below 50 mbar, by means of an inert gas mixture, substantially reduces the proportion of high boilers as by-product of the conversion of the epoxide to the ketone.

TABLE 6

Overview of the partial pressures and the proportions of reaction products resulting therefrom.

| Example | Partial pressure (CO) in mbar | Total pressure in the reactor in bar | Selectivity in mol-% CDON | Selectivity mol % High boilers |
|---|---|---|---|---|
| 1 | 83 | 3.2 | 6.8 | 17 |
| 2 | 59 | 3.2 | 37.4 | 16.5 |
| 3* | 27 | 3.2 | 89.9 | 2 |
| 4* | 21 | 1.2 | 88.5 | 2.9 |
| 5* | 8 | 1.2 | 90.2 | 2.3 |

*inventive

The invention claimed is:

1. A method, comprising:
    continuously producing a ketone from a compound comprising at least one epoxide group, in a device comprising at least one fixed bed reactor, wherein the at least one fixed bed reactor contains a catalyst composition comprising at least one noble metal and at least one metal oxide, wherein at least one non-reactive gas is introduced in the reactor, and wherein
    a. the pressure in the reactor upstream of the catalyst is at least 1.2 bar,
    b. the gas phase of the reactor has a maximum hydrogen partial pressure of 0.2 bar, and
    c. a carbon monoxide partial pressure of 50 mbar or less is set in a gas phase of the reactor downstream of the catalyst by introducing at least one inert gas.

2. The method according to claim 1, wherein a carbon monoxide partial pressure of 30 mbar or less is set in the gas phase of the fixed bed reactor.

3. The method according to claim 1, wherein the metal oxide of the catalyst system comprises titanium dioxide, zirconium dioxide, or mixtures thereof, or consists of titanium dioxide, zirconium dioxide, or mixtures thereof.

4. The method according to claim 1, wherein the total pressure in the reactor is 4 bar or less.

5. The method according to claim 1, wherein a ratio of the amount of inert gas and the amount of the compound comprising epoxide group is at least 0.5.

6. The method according to claim 1, wherein at least one further fixed bed reactor is downstream of the fixed bed reactor.

7. The method according to claim 6, wherein offgas is introduced in countercurrent between the fixed bed reactors.

8. The method according to claim 1, wherein the compound comprising at least one epoxide group is a cycloaliphatic compound having 4 to 20 carbon atoms.

9. The method according to claim 7, wherein the compound comprising at least one epoxide group comprises monoepoxycyclododecane.

10. A method for synthesizing g lactam, the method comprising:
    a. rearranging at least one compound comprising an epoxide group to a ketone,
    b. oximating the ketone to an oxime, and
    c. rearranging, by Beckmann rearrangement, the oxime to the lactam,
    wherein the rearrangement a. is conducted according to the method of claim 1.

11. The method according to claim 1, wherein the gas phase of the reactor in b. has no hydrogen.

12. The method according to claim 1, wherein the total pressure in the reactor is 2 bar or less.

13. The method according to claim 1, wherein a proportion of high-boiling by-products is less than 5% by weight, based on the epoxide converted.

* * * * *